US009957202B2

(12) United States Patent
Martin et al.

(10) Patent No.: US 9,957,202 B2
(45) Date of Patent: May 1, 2018

(54) PROCESS AND SUPPLY UNIT FOR RESTABILIZING FREE-RADICALLY POLYMERIZABLE MONOMERS

(71) Applicant: BASF SE, Ludwigshafen (DE)

(72) Inventors: Friedrich-Georg Martin, Heidelberg (DE); Oliver Odenwald, Dielheim (DE)

(73) Assignee: BASF SE, Ludwigshafen (DE)

( * ) Notice: Subject to any disclaimer, the term of this patent is extended or adjusted under 35 U.S.C. 154(b) by 216 days.

(21) Appl. No.: 14/261,932

(22) Filed: Apr. 25, 2014

(65) Prior Publication Data

US 2014/0319417 A1    Oct. 30, 2014

Related U.S. Application Data

(60) Provisional application No. 61/816,175, filed on Apr. 26, 2013.

(30) Foreign Application Priority Data

Apr. 26, 2013 (DE) .................. 10 2013 007 298

(51) Int. Cl.
*C07B 63/04* (2006.01)
*B01J 19/00* (2006.01)
*B01J 4/00* (2006.01)

(52) U.S. Cl.
CPC .............. *C07B 63/04* (2013.01); *B01J 4/001* (2013.01); *B01J 19/002* (2013.01); *B01J 2219/00272* (2013.01)

(58) Field of Classification Search
CPC ......... C07B 63/04; B01J 19/002; B01J 4/001; B01J 2219/00272
See application file for complete search history.

(56) References Cited

U.S. PATENT DOCUMENTS 6,294,056 B1 *   9/2001   Matsumoto ............ B01D 3/008
                                                          202/158
6,517,057 B1     2/2003   Aichinger et al.
(Continued)

FOREIGN PATENT DOCUMENTS

DE          198 22 492 A1      8/1999
DE     10 2005 042 607 A1      3/2007
(Continued)

OTHER PUBLICATIONS

International Search Report dated Jul. 7, 2014 in PCT/EP2014/058414.

*Primary Examiner* — Peter F Godenschwager
*Assistant Examiner* — Andrew J. Oyer
(74) *Attorney, Agent, or Firm* — Oblon, McClelland, Maier & Neustadt, L.L.P.

(57) ABSTRACT

The present invention relates to a process for restabilizing free-radically polymerizable monomers. The process comprises the steps: (a) introduction of a solution of an inhibitor of the free-radical polymerization by means of an inert pressurized gas into a vessel (1) comprising the monomers via a line (10) which comprises an ascending region, and (b) mixing of the contents of the vessel and the inhibitor solution by blowing gas through the line (10). In step (a), the flow velocity of the pressurized gas is set so that plug flow or annular flow is obtained as flow regime of the inhibitor solution and in step (b) the superficial gas velocity is set to ≥0.1 mm/s. The present invention further relates to a supply unit (11) for carrying out the process.

9 Claims, 2 Drawing Sheets

(56) References Cited

U.S. PATENT DOCUMENTS

2008/0200623 A1    8/2008   Weismantel et al.
2009/0166175 A1*   7/2009   Waibel .................. B01D 3/007
                                                                   203/49

FOREIGN PATENT DOCUMENTS

WO       WO 99/24161 A1    5/1999
WO       WO 99/59717 A1   11/1999

\* cited by examiner

PROCESS AND SUPPLY UNIT FOR RESTABILIZING FREE-RADICALLY POLYMERIZABLE MONOMERS

The present invention relates to a process for restabilizing free-radically polymerizable monomers and a supply unit for carrying out the process.

Monomers which are free-radically polymerizable, e.g. (meth)acrylic acid and the derivatives thereof, are handled in relatively large vessels, for example in storage tanks or columns, in the chemical industry. There is a risk here that polymerization of the monomers can be undesirably started by an increase in temperature, failure of cooling, stabilizer inactivity or lack of stabilizer. This could result in a considerable danger to the production plant if the incipient polymerization cannot be quickly and effectively suppressed and stopped. The use of polymerization inhibitors for this purpose is known. It is in this case essential that the polymerization inhibitors are added in the required amount and sufficient mixing with the monomers can be brought about. Conventional introduction of the polymerization inhibitors and mixing by means of a pump is disadvantageous because the supply of power necessary for operation of a pump is not ensured in the case of an emergency. WO 99/59717 therefore describes a supply system in the case of which an inhibitor solution is introduced by means of a pressurized gas into, for example, a storage tank comprising the monomers. The mixing of monomers and inhibitor solution is effected by further introduction of inert gas such as nitrogen. However, it has been found that the supply system described in WO 99/59717 is still capable of improvement.

It is therefore an object of the present invention to provide a process for restabilizing free-radically polymerizable monomers and an apparatus for carrying out the process which ensures that the inhibitor solution is introduced essentially completely into the monomer vessel and sufficient mixing of monomer vessel contents and inhibitor solution can be brought about.

This object is achieved by a process for restabilizing free-radically polymerizable monomers, which comprises the steps
a) introduction of a solution of an inhibitor of the free-radical polymerization by means of an inert pressurized gas into a vessel comprising the monomers via at least one line (feed line) which comprises an ascending region and at its end means for introducing the inhibitor solution and for blowing gas into the vessel, and
b) mixing of the contents of the vessel and the inhibitor solution by blowing gas through the line,
where the flow velocity of the pressurized gas in step (a) is set so that plug flow or annular flow is obtained as flow regime of the inhibitor solution in the ascending region of the line and the superficial gas velocity in the vessel in step (b) is set to ≥0.1 mm/s.

The inhibitor solution is provided in the form of a supply unit comprising
(a) a vessel for the inhibitor solution having an offtake tube extending into the inhibitor solution,
(b) at least one pressurized gas reservoir which is connected to the vessel for the inhibitor solution via a gas feed line,
(c) means for reducing the pressure on the pressurized gas reservoir,
(d) means in the gas feed line for setting the superficial gas velocity and
(e) means for connecting the offtake line to the line to the monomer vessel.

For the present purposes, "restabilizing" refers to inhibition of a started polymerization of free-radically polymerizable monomers and stabilization of the remaining monomers against further polymerization. However, the expression "restabilizing" also comprises the after-stabilization of monomers without the polymerization having already started and also the stabilization of monomers when contamination with materials which can trigger or support a polymerization is present or is to be feared or when a fire has broken out or there is a risk of a fire.

For the present purposes, the term "vessel" refers to a vessel of any shape, e.g. a cylindrical, rectangular, square or spherical tank. It is preferably an essentially cylindrical vessel, in particular an upright cylindrical vessel. The ratio of height to diameter of the upright cylindrical vessel is generally ≥0.1 and is preferably in the range from 0.1 to 8, in particular from 0.1 to 5. The tank volume is, in particular, in the range from 20 to 10 000 $m^3$, corresponding to a height of the tank of from 3 to 20 m.

The vessel for the inhibitor solution is advantageously an approximately cylindrical vessel, preferably made of stainless steel. The pressurized gas reservoir generally has means for reducing the pressure which regulate the exit of gas at the pressurized gas reservoir. On opening the means for reducing the pressure, pressurized gas flows via the gas feed line into the vessel for the inhibitor solution and pushes the inhibitor solution through the offtake line which extends into the inhibitor solution, advantageously virtually into the bottom of the vessel for the inhibitor solution, into the line leading to the vessel comprising the monomers. This line preferably comprises at least one horizontal and/or descending part and an ascending, in particular essentially vertical, part. It can be advantageous to make the diameter of the horizontal or descending part of the line greater than the diameter of the ascending line. This minimizes the pressure drop and introduction time for the inhibitor solution, especially when the supply unit is, for safety reasons, arranged at a relatively great distance (20-100 m) from the monomer tank. The line preferably has essentially the same diameter over its entire length.

The means for introducing the inhibitor solution and the mixing gas is preferably a tube which ends in the region of the bottom of the monomer vessel. The tube is advantageously closed off by a bursting disk, in particular a dead-space-free bursting disk, which is destroyed when the supply unit is operated.

In a further embodiment, the means for introducing the inhibitor solution and the mixing gases is a telescopic lance. Such a telescopic lance is described in WO 99/24161, which is fully incorporated by reference.

To ensure that the total inhibitor solution present in the line is transported into the tank, the flow velocity of the pressurized gas is set so that plug flow or annular flow is obtained as flow regime of the inhibitor solution, especially in the ascending part of the line. The establishment of plug flow or annular flow depends, inter alia, on the flow velocity of the pressurized gas and the line diameter. The flow velocity of the pressurized gas is preferably in the range 6-12 m/s, in particular 8-12 m/s. Determination of the flow velocity is known to those skilled in the art. For example, it can be carried out by the methods described in Multiphase Science and Technology, Chapter 1, pages 1-94, by A. E. Dukler and Y. Taitel.

The inhibitor solution is preferably introduced in the region of the bottom of the vessel (distance from the bottom preferably 1/100 to 1/10 of the vessel height; in the case of spherical vessels, at a distance of 1/100 to 1/10 from the wall).

However, the introduction can also be effected at a greater distance from the bottom or the wall.

The ascending part of the feed line extends, in particular, over a height of from 1/10 to 10/10 of the vessel height.

For the inhibitor solution to inhibit a started polymerization or prevent commencement of a polymerization, it has to be effectively mixed with the contents of the monomer vessel. For this purpose, gas is blown into the region of the vessel bottom. The gas bubbles ascending in the monomer liquid present in the vessel bring about vertical circulation of the vessel contents, so that mixing occurs (provided that the viscosity of the vessel contents is <350 mPas, which is generally the case for the monomer liquids and temperatures coming into question here). Mixing is particularly effective when the line is arranged close to the wall and the gas exits in the region of the bottom of the vessel. However, the inhibitor solution can fulfill its purpose only when mixing occurs sufficiently quickly and uniformly. It has been found that a minimum superficial gas velocity in the vessel of ≥0.1 mm/s is necessary for this purpose. In general, the superficial gas velocity is in the range 0.1-20 mm/s, in particular 0.1-10 mm/s. To achieve this, the gas feed line is provided with means which connects the pressurized gas reservoir to the vessel for the inhibitor solution. This means is preferably an orifice plate which has, in particular, a configuration based on DIN ISO 5167-2. The orifice plate comprises an opening. The size of the opening should be selected as a function of the diameter of the gas feed line and the size of the vessel. In addition, a constant mass flow of gas is brought about by this means.

The superficial gas velocity can be calculated according to the following formula:

$$u_{g0} = \frac{\dot{V}_g}{A_B} = \frac{\dot{m}_g}{\rho_g \cdot A_B}$$

where $\dot{V}_g$ is the volume flow of the gas, $A_B$ is the cross-sectional area of the monomer vessel, $\dot{m}_g$ is the mass flow of the gas and $\rho_g$ is the gas density.

The amount of pressurized gas required to effect mixing of inhibitor solution and vessel contents depends on the size of the vessel and on the volume of the monomer liquid present in the vessel. Should one supply unit not be sufficient to maintain the minimum superficial gas velocity for the time required for mixing, it is advantageous to use either a supply unit having one or more additional pressurized gas reservoirs or one or more further supply units connected in series. To set the superficial gas velocity, it can be necessary to use one or more further supply units connected in parallel.

As pressurized gas, use is made of, in particular, nitrogen or a mixture of nitrogen and oxygen having a volume ratio of from 5 to 21% by volume, in particular from 5 to 8% by volume, of oxygen.

The supply unit of the invention can comprise one or more, preferably from 1 to 6, pressurized gas reservoirs which optionally have means for reducing the pressure. The supply unit is particularly preferably configured as a mobile unit.

The end of the offtake line is provided with means for connecting the offtake line to the line to the tank.

In the case of the line extending into the vessel, it has to be taken into account that inhibitor-depleted or inhibitor-free monomer, which can easily polymerize and therefore form encrustations, can be formed in dead spaces, etc., or by condensation of monomer on cold surfaces. The risk of formation of encrustations can be reduced or even avoided by continuously flushing the line with a small stream of nitrogen or a mixture of nitrogen and oxygen (5-21% by volume of oxygen), with the stream being fed into the line via a valve. If the gas pressure goes below a particular value, it is advantageous to trigger an alarm signal.

As an alternative, the encrustations can be prevented by the abovementioned bursting disk. Here, the line extending into the tank is closed off at its end by a bursting disk, preferably a dead-space-free bursting disk, which is destroyed when the supply unit is operated. A further alternative is the use of the abovementioned telescopic lance which when not being used is located above the surface of the liquid in the vessel and is protected against monomer vapor and liquid.

The process of the invention and the supply unit of the invention are suitable for bringing about effective stabilization of free-radically polymerizable monomers or for inhibiting a started polymerization of free-radically polymerizable monomers. Free-radically polymerizable monomers are generally vinyl monomers. Examples are acrylic acid, methacrylic acid, acrylic esters, methacrylic esters, substituted acrylic esters and methacrylic esters, e.g. hydroxyalkyl acrylates and methacrylates, itaconic acid and the derivatives thereof mentioned for acrylic acid, maleic acid and the derivatives thereof mentioned for acrylic acid, styrene and derivatives thereof, N-vinyllactams such as N-vinylpyrrolidone, etc.

Suitable inhibitors are, for example, phenothiazine and derivatives thereof, e.g. N-alkylated phenothiazines, for example N-benzylphenothiazine or N-(1-phenylethyl)phenothiazine, N-(diphenylmethyl)phenothiazine, N,N'-dimethylphenazine, phenoxazine, promazine and the hydrochloride thereof, carbazole, N-ethylcarbazole, hydroquinones and derivatives thereof, e.g. hydroquinone ethers, for example hydroquinone monomethyl ether (MeHQ), alkyl-substituted hydroquinones, for example mono-t-butylhydroquinone, 2-5-di-t-butylhydroquinone or toluhydroquinone.

The inhibitors are employed as a solution in an organic solvent. Suitable solvents are, in particular, acetone, ethyl acetate and preferably N-alkylpyrrolidones such as N-methylpyrrolidone (NMP) and/or N-ethylpyrrolidone. A particularly preferred inhibitor solution is a solution of phenothiazine in NMP. It is also advantageous for the inhibitor content of the solution, based on the weight of the inhibitor solution, to be from ≥10% by weight to 55% by weight. Particular preference is given to a 30-40% strength by weight solution of phenothiazine in NMP, which can optionally comprise up to 10% by weight of hydroquinone ethers, in particular MEHQ.

The required amount of inhibitor depends on the size of the tank, with the calculation of the amount being based on 100% fill height. The amount of inhibitor also depends on the inhibitor used and the monomers to be restabilized. A concentration of from about 200 ppm to 300 ppm of phenothiazine is in most cases able to inhibit the polymerization of the monomers. It has been found that in most cases concentrations of from 50 to 1000 ppm of phenothiazine are sufficient to inhibit the polymerization to such an extent that it no longer represents a hazard. Should the amount of inhibitor solution in one supply unit not be sufficient to stabilize the monomers, one or more further supply units connected in series is/are used.

A 35% strength solution of phenothiazine in N-methylpyrrolidone has sufficient flowability for practical use at temperatures of −10° C. or above. It is nevertheless advantageous to store the solution and the supply unit at temperatures of >0° C. A 35% strength solution of phenothiazine in N-methylpyrrolidone (w/w) has a storage life of about five years under normal storage conditions (0-60° C.).

The process of the invention and the supply unit of the invention make it possible to restabilize free-radically polymerizable monomers in a reliable, quick and economical way and are independent of energy sources and mixing devices, which is of particular importance in emergencies with interruption of the power supply. The inhibitor can be quickly introduced into the tank and mixed with the tank contents and a free-radical polymerization can in this way be reliably inhibited even in an advanced state.

The invention will be illustrated by an example with reference to the drawings. In the drawings:

FIG. 1 schematically shows the supply unit connected to a tank,

Figure 1:
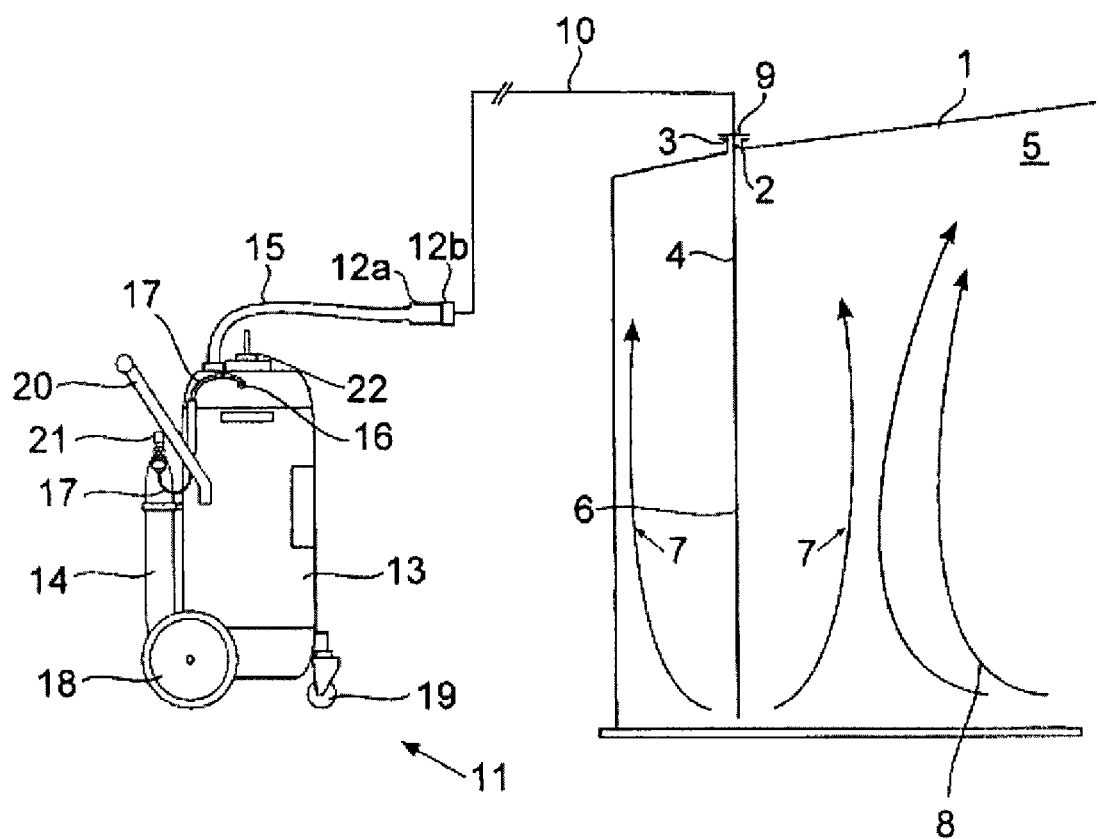

FIG. 1 schematically shows a supply unit 11 according to the invention connected to a vessel 1. The vessel is configured as tank 1. Tank 1 has an opening 2 having a vertical connecting flange 3. A tube 4 of an apparatus for introducing the inhibitor solution and the mixing gas into the interior space 5 of the tank 1 projects through the opening 2. The tube 4 with its end 6 located in the vicinity of the bottom of the tank 1 serves for introduction of inhibitor solution and mixing gas. The tube 4 is provided at its other end with a support flange 9 for fastening to the flange 3 of the tank 1, with fastening being able to be effected directly or with use of an intermediate flange. A feed line 10 for the inhibitor solution and the mixing gas to be introduced into the interior space 5 is connected to this tube 4. The feed line 10 comprises an essentially horizontal part and an essentially vertically ascending part. As an alternative, the horizontal part can also be descending.

The supply unit 11 according to the invention is connected to the feed line 10 only in a dangerous situation, for which purpose coupling means 12a and 12b are provided. The inhibitor solution is present in the vessel 13 of the supply unit 11 and said vessel is connected to two pressurized gas reservoirs in the form of propellant gas bottles 14. Owing to the side view, only one of the two propellant gas bottles 14 can be seen. Within the stock space of the vessel 13, there is an offtake tube which with its one end extends virtually to the bottom of the vessel 13, while the other end is connected to the hose 15. As a result of opening of the propellant gas bottles 14, pressurized gas is introduced via the pressurized gas feed lines 17 into the vessel 13, so that the inhibitor solution is driven out from the vessel 13 via the offtake tube and is introduced through the tube 4 into the tank contents. Gas from the propellant gas bottles 14 is subsequently introduced via the vessel 13 and the feed line 10 into the tank 1 in such a way that the superficial gas velocity is ≥0.1 m/s. The ascending gas bubbles bring about an upward-directed flow in the interior space 5 of the tank 1, as indicated by the arrows 7. This upward flow in the region of the tube 4 also induces corresponding flow in adjacent regions, represented by the arrows 8. Introduction of the gas brings about intensive mixing of the tank contents with the inhibitor solution. To generate particularly effective mixing, the end 6 of the tube 4 is arranged in the vicinity of a wall of the tank 1 and in particular in the vicinity of the bottom of the tank 1. As an alternative, the tube 4 can also run through the side wall of the tank 1 into the interior space 5 of the tank.

The supply unit 11 is arranged at a distance from the tank 1. For safety reasons, the distance between the supply unit 11 and the tank 1 should be at least 20 m. However, to ensure an acceptable introduction time, the distance should be not more than 200 m.

The coupling means 12a is connected via a flexible hose 15 to the offtake tube, while the coupling means 12b is fastened to the end of the feed line 10. The vessel 13 is provided with rollers 18, 19 and a handle 20, so that the supply unit 11 can be moved by hand. Here, the wheels 18 essentially carry the weight of the supply unit and the wheel 19 is configured as steering roller. Between the vessel 13 and the propellant gas bottles 14 there are pressure-reducing valves 21 by means of which the gas leaving the propellant gas bottles 14 under high pressure is depressurized to a constant pressure of about 10 bar. The vessel 13 has a feed opening whose closure 22 is provided with an emergency pressure relief valve. If the supply unit 11 is actuated, pressure builds up in the tube 4. As a result, the inhibitor solution is pushed through the tube 4 into the interior space 5 of the tank. The flow velocity of the pressurized gas is set so that plug flow or annular flow is obtained as flow regime of the inhibitor solution in the vertically ascending part of the feed line 10. This ensures that all of the inhibitor solution present in the line 10 is transported into the tank 1. The flow velocity is for this purpose set to a value in the range from 6 to 12 m/s, in particular to a value in the range from 8 to 12 m/s.

Since the amount of inhibitor solution required is a function of the size of the tank 1, it is necessary in the case of large tanks 1 to connect more than one supply unit 11 to the tank 1. For this purpose, a plurality of supply units 11 can be connected in parallel. Depending on the mixing gas requirement, the supply unit 11 can comprise one or more pressurized gas reservoirs 14.

Figure 2:
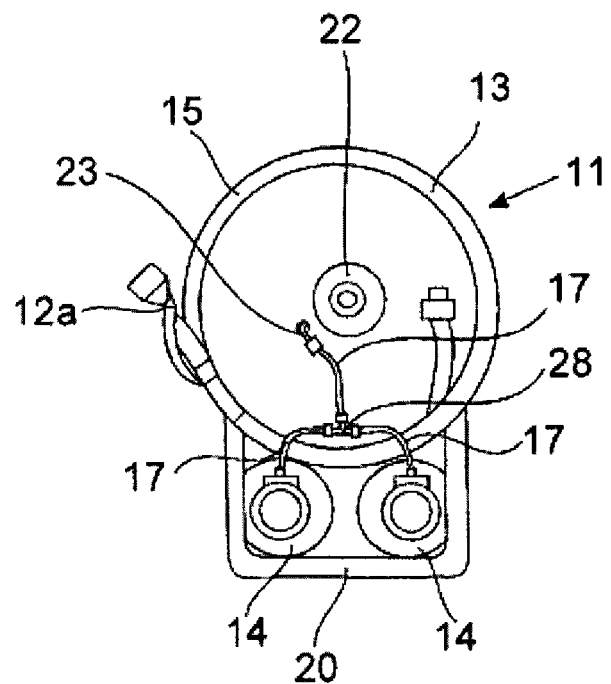
FIG. 2 shows a plan view of the supply unit depicted in FIG. 1.

FIG. 2 shows a plan view of the set-up supply unit. The vessel 13, the propellant gas bottles 14 fastened thereto and the handle 20 can be seen. The hose 15, whose end is provided with the coupling means 12a, is wound around the vessel 13. The pressurized gas feed lines 19 of the two propellant gas bottles 14 run via a three-way connection 28 into a joint feed line 17. The joint feed line 17 conveys the pressurized gas from the two propellant gas bottles 14 via a connecting piece 23 into the vessel.

Figure 3:
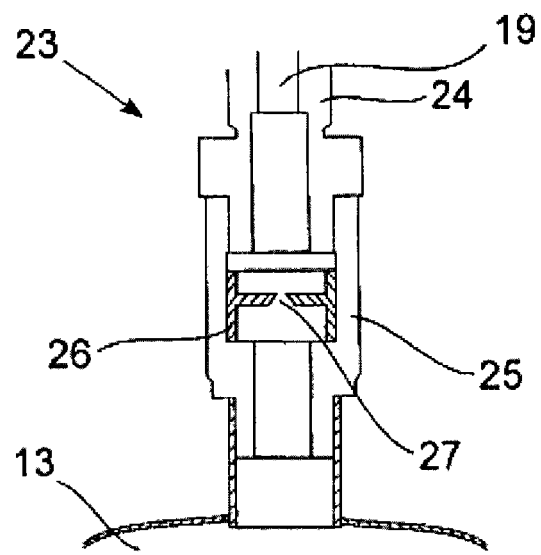
FIG. 3 shows a detailed view of the valve shown in FIG. 2.

In FIG. 3, the connecting piece 23 which connects the joint feed line 17 to the vessel 13 is shown in detail. The connecting piece 23 comprises an upper part 24 and a lower part 25, with the lower part 25 enclosing the upper part 24. The pressurized gas feed line 17 ends in the upper part 24. Between the upper part 24 and the lower part 25, there is an orifice plate 26 having an opening 27. The size of the opening 27 is selected according to the diameter of the feed line 10 and the size of the tank 1. This enables the required superficial gas velocity to be set. In particular, the superficial gas velocity is set to a value of ≥0.1 mm/s by selection of the diameter of the opening. This ensures sufficiently rapid and uniform mixing of the inhibitor solution with the contents of the tank 1.

LIST OF REFERENCE NUMERALS

1 Tank
2 Opening
3 Connecting flange
4 Tube
5 Interior space of the tank
6 Tube end 7 Upward-directed flow in the region of the tube
8 Upward-directed flow in regions adjacent to the tube
9 Support flange
10 Feed line
11 Supply unit
12 Coupling means
13 Vessel for the inhibitor solution
14 Pressurized gas reservoir
15 Hose
16 Connection for a pressurized gas feed line
17 Pressurized gas feed line
18 Wheel
19 Wheel
20 Handle
21 Pressure-reducing valve
22 Closure for the feed opening of the pressurized gas reservoir
23 Connecting piece
24 Upper part of the valve
25 Lower part of the valve
26 Orifice plate
27 Opening of the orifice plate
28 Three-way connection

The invention claimed is:

1. A process for stabilizing free-radically polymerizable monomers, comprising:
   a) introducing a solution of an inhibitor of the free-radical polymerization by means of an inert pressurized gas into a vessel comprising the monomers via at least one line which comprises an ascending region and at its end means for introducing the inhibitor solution and for blowing gas into the vessel; and
   b) mixing of the contents of the vessel and the inhibitor solution by blowing gas through the line, wherein
   the flow velocity of the pressurized gas in the introducing (a) is set so that plug flow or annular flow is obtained as flow regime of the inhibitor solution in the ascending region of the line and the superficial gas velocity in the vessel in the mixing (b) is set to from 0.1 to 20 mm/s, and
   the flow velocity of the pressurized gas in the introducing (a) is set to from 6 to 12 m/s,
   and wherein the supply unit comprises:
      (a) a vessel for the inhibitor solution having an offtake tube extending into the inhibitor solution;
      (b) at least one pressurized gas reservoir which is connected to the vessel for the inhibitor solution via a gas feed line;
      (c) means for reducing the pressure on the pressurized gas reservoir;
      (d) means in the gas feed line for setting the superficial gas velocity; and
      (e) means for connecting the offtake line to the line to the vessel,
      wherein the (d) means for setting the superficial gas velocity has a connecting piece comprising an orifice plate, where the superficial gas velocity in the vessel in the mixing (b) is set to from 0.1 to 20 mm/s by means of the orifice plate.

2. The process according to claim 1, wherein the inhibitor solution and the gas stock are provided by at least one supply unit which comprises a vessel for the inhibitor solution and at least one pressurized gas reservoir.

3. The process according to claim 2, wherein the supply unit is arranged at a distance from the vessel and is connected to the vessel via the line.

4. The process according to claim 1, wherein the line runs from the supply unit to the vessel through the lid of the monomer vessel.

5. The process according to claim 1, wherein a plurality of supply units are connected in series or in parallel to the line.

6. The process according to claim 1, wherein the supply unit comprises one to six pressurized gas reservoirs.

7. The process according to claim 1, wherein the supply unit is configured as a mobile unit.

8. The process according to claim 1, wherein the vessel is an upright cylindrical vessel, wherein a ratio of height to diameter of the upright cylindrical vessel is from 0.1 to 8.

9. The process according to claim 8, wherein in the introducing (a), the inhibitor solution is introduced in a region of the bottom of the vessel, wherein the region is located at a distance from the bottom of $1/100$ to $1/10$ of the vessel height and at a distance of $1/100$ to $1/10$ from the vessel wall.

* * * * *